United States Patent [19]

Yamamoto et al.

[11] Patent Number: 5,834,621

[45] Date of Patent: Nov. 10, 1998

[54] NOVEL SULFUR-CONTAINING COMPOUND AND METHOD FOR PREPARING THE SAME

[75] Inventors: Katsumasa Yamamoto; Masahito Nakano; Michio Suzuki, all of Hyogo, Japan

[73] Assignee: Sumitomo Seika Chemicals Co., Ltd., Hyogo, Japan

[21] Appl. No.: 809,929

[22] PCT Filed: Aug. 7, 1996

[86] PCT No.: PCT/JP96/02244

§ 371 Date: Apr. 3, 1997

§ 102(e) Date: Apr. 3, 1997

[87] PCT Pub. No.: WO97/08139

PCT Pub. Date: Mar. 6, 1997

[30] Foreign Application Priority Data

Aug. 22, 1995 [JP] Japan .................................. 7-237799

[51] Int. Cl.[6] .................................................. C07C 69/52
[52] U.S. Cl. ................................ 560/221; 568/57; 568/58
[58] Field of Search .............................. 560/221; 568/57, 568/58

[56] References Cited

U.S. PATENT DOCUMENTS

| | | |
|---|---|---|
| 4,605,774 | 8/1986 | Baron et al. . |
| 4,689,387 | 8/1987 | Kajimoto et al. . |
| 4,775,733 | 10/1988 | Kanemura et al. . |
| 5,077,436 | 12/1991 | Yoshikawa et al. . |

FOREIGN PATENT DOCUMENTS

| | | |
|---|---|---|
| 60-199016 | 10/1985 | Japan . |
| 415249 | 3/1992 | Japan . |
| 54404 | 1/1993 | Japan . |

OTHER PUBLICATIONS

Chem Abs 121: 134916 (1994).

*Primary Examiner*—Paul J. Killos
*Attorney, Agent, or Firm*—Birch, Stewart, Kolasch & Birch, LLP

[57] ABSTRACT

A novel sulfur-containing compound represented by the general formula (I):

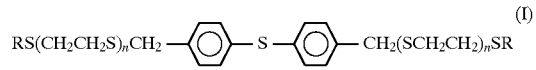

wherein n is an integer from 0 to 2; R represents a hydrogen atom, a vinyl group, a methacryloyl group, a vinylbenzyl group, a glycidyl group, an acryloyl group or an allyl group; and the case where n is 0 and R is a hydrogen atom is excluded, and a method for preparing said sulfur-containing compound. The novel sulfur-containing compound of the present invention can be copolymerized with various copolymerizable compounds to yield excellent hardened products of high refractive index. The novel sulfur-containing compound of the present invention can therefore be used as a very useful monomer for the production of optical materials, paints, adhesives, sealants, etc. having excellent properties.

19 Claims, No Drawings

NOVEL SULFUR-CONTAINING COMPOUND AND METHOD FOR PREPARING THE SAME

TECHNICAL FIELD

The present invention relates to a novel sulfur-containing compound and a method for its preparation, more specifically to a novel sulfur-containing compound useful as a polymerization starting material for optical materials, such as plastic lenses for eyeglasses, Fresnel lenses, lenticular lenses, optical disc substrates, plastic optical fiber, prism sheets for LCD, photoconductive plates and diffusion sheets; paints; adhesives; sealants; and other materials, especially as a polymerization starting material (monomer) for optical materials, and a method for its preparation.

BACKGROUND ART

In recent years, resins for organic optical materials have been commonly used for various purposes, because they are lighter and easier to handle than glass etc.

Of such resins for organic optical materials, polystyrene resin, polymethyl methacrylate resin, polycarbonate resin, diethylene glycol diallylcarbonate resin, etc. have traditionally been used widely.

These conventional resins for organic optical materials are not always satisfactory, however, because they have some drawbacks, including low refractive index, great double refraction and high dispersive power, and because their heat resistance and impact resistance are poor.

Diethylene glycol diallylcarbonate resin (CR-39) etc. used as lens materials, in particular, are faulty in case that the lens made thereof has great edge thickness and center thickness due to the low refractive index (1.50), resulting in poor lens appearance and increased weight.

To resolve these problems, various methods have been proposed, mainly with the aim of increasing the refractive index. For example, Japanese Patent Examined Publication No. 5/4404 discloses a resin wherein a halogen is introduced to an aromatic ring. It should be noted, however, that the resin obtained by that method has a specific gravity of as high as 1.37, though having an increased refractive index of 1.60, and is unsatisfactory in terms of lens lightness, a major requirement for plastic lenses.

Japanese Patent Examined Publication No. 4/15249 and Japanese Patent Laid-Open No. 60/199016 disclose a technology for preparation of a resin by polymerization of an isocyanate compound and polythiol. However, said resin also has a specific gravity of not less than 1.30, though having an increased refractive index of 1.60. As another drawback, the resin's relatively low polymerization temperature and high polymerization rate hamper heat control during polymerization, resulting in significant optical strain.

DISCLOSURE OF THE INVENTION

The present invention was developed in view of the above circumstances. Accordingly, the object of the present invention is to provide a novel sulfur-containing compound as a monomer suitable for preparation of a resin having a high refractive index, and a method for its preparation.

Specifically, the gist of the present invention concerns:
(1) A novel sulfur-containing compound represented by the following general formula (I):

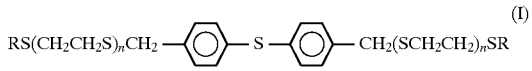

wherein n is an integer from 0 to 2; R represents a hydrogen atom, a vinyl group, a methacryloyl group, a vinylbenzyl group, a glycidyl group, an acryloyl group or an allyl group; and the case where n is 0 and R is a hydrogen atom is not included;

(2) The novel sulfur-containing compound described in item (1) above, wherein R in the general formula (I) is a hydrogen atom, a vinyl group, a methacryloyl group, a vinylbenzyl group, or a glycidyl group;

(3) A method for preparing a sulfur-containing compound represented by the following general formula (Ia):

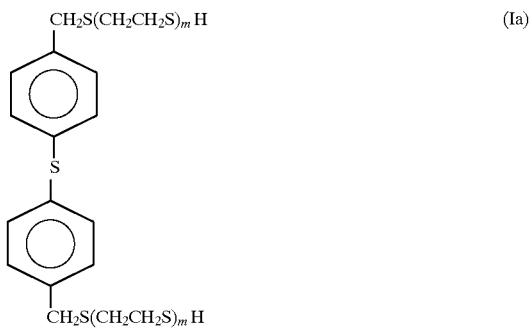

wherein m is an integer of 1 or 2,
characterized by reacting, in the presence of a base, a bis(4-halogenomethylphenyl) sulfide represented by the following general formula (II):

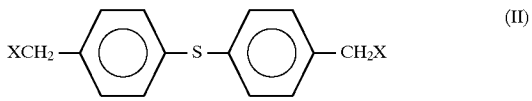

wherein X is a chlorine atom, a bromine atom or an iodine atom with a dithiol represented by the following general formula (III):

wherein m is an integer of 1 or 2;

(4) A method for preparing a sulfur-containing compound represented by the following general formula (Ia):

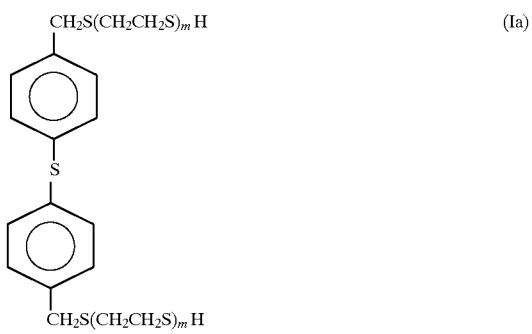

wherein m is an integer of 1 or 2,
characterized by reacting, in the presence of a base, a bis(4-halogenomethylphenyl) sulfide represented by the following general formula (II):

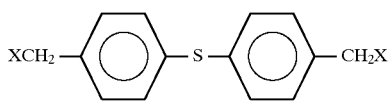  (II)

wherein X is a chlorine atom, a bromine atom or an iodine atom with a mercaptoalcohol represented by the following general formula (IV):

  (IV)

wherein m is an integer of 1 or 2; treating the reaction product with thiourea in the presence of a mineral acid to form an isothiuronium salt; and hydrolyzing the salt;

(5) A method for preparing a sulfur-containing compound represented by the following general formula (Ib):

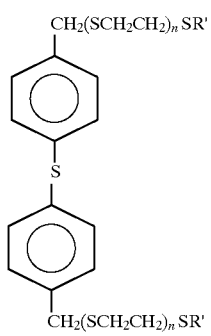  (Ib)

wherein n is an integer from 0 to 2; R' is a vinyl group, a methacryloyl group, a vinylbenzyl group, a glycidyl group, an acryloyl group or an allyl group,
characterized by reacting, in the presence of a base, an aromatic ring-containing dithiol represented by the following general formula (V):

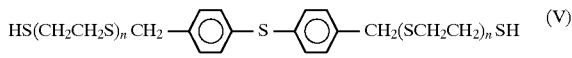  (V)

wherein n is an integer from 0 to 2
with a halogen derivative represented by the following general formula (VI):

R'X  (VI)

wherein R' is a vinyl group, a methacryloyl group, a vinylbenzyl group, a glycidyl group, an acryloyl group or an allyl group; and X is an chlorine atom, a bromine atom or an iodine atom; and (6) A method for preparing a sulfur-containing compound represented by the following general formula (Ic):

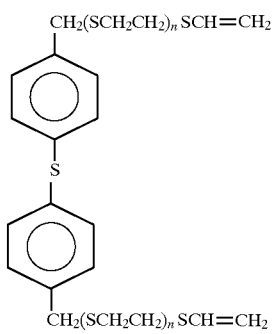  (Ic)

wherein n is an integer from 0 to 2 characterized by reacting, in the presence of a base, an aromatic ring-containing dithiol represented by the following general formula (V):

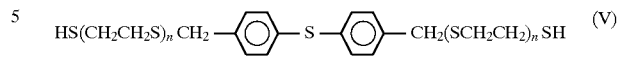  (V)

wherein n is an integer from 0 to 2 with a dihalogenoethane represented by the following general formula (VII):

$XCH_2CH_2X$  (VII)

wherein each of the two X radicals, which may be identical or different, is a chlorine atom, a bromine atom or an iodine atom; and dehydrohalogenating the reaction product in the presence of a base to introduce a vinyl group at the terminal.

BEST MODE FOR CARRYING OUT THE INVENTION

First, the novel sulfur-containing compound of the present invention is described in detail below.

The novel sulfur-containing compound of the present invention is represented by general formula (I) below:

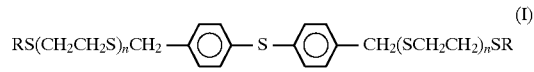  (I)

With respect to general formula (I) above, R represents a hydrogen atom, a vinyl group, a methacryloyl group, a vinylbenzyl group, a glycidyl group, an acryloyl group or an allyl group, preferably a hydrogen atom, a vinyl group, a methacryloyl group, a vinylbenzyl group or a glycidyl group. The two R radicals may be identical or different.

With respect to general formula (I), n represents an integer from 0 to 2. When n is 0 and R is hydrogen atom, the compound is excluded from the scope of the novel sulfur-containing compound of the present invention.

Although the novel sulfur-containing compound of the present invention can be preferably prepared by the preparation method of the present invention described below, it is not limited to the products obtained by said preparation method. The preparation method of the present invention can be divided according to the type of R etc. into four embodiments (first through fourth). The preparation method of the present invention is hereinafter described in detail.

The novel sulfur-containing compound of the present invention, represented by general formula (I) above, wherein R is a hydrogen atom, i.e., a novel dithiol compound, can be synthesized by, for example, the method schematized by the formula below (first embodiment).

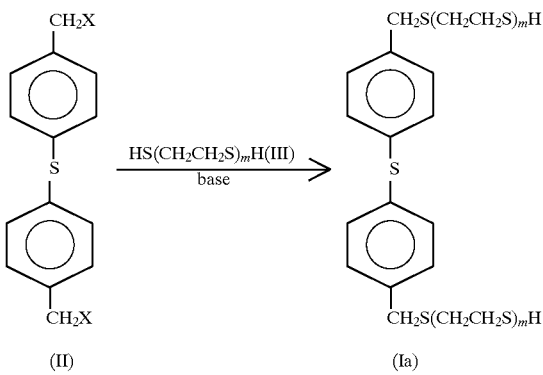

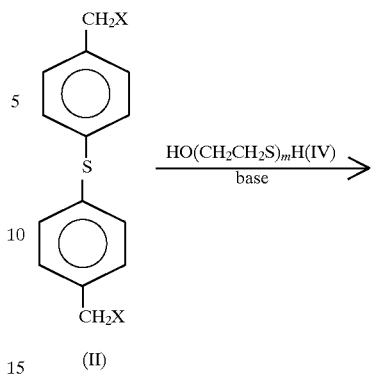

wherein m represents an integer of 1 or 2; X represents a chlorine atom, a bromine atom or an iodine atom.

Specifically, the desired novel sulfur-containing compound can be obtained by reacting a bis(4-halogenomethylphenyl) sulfide represented by general formula (II) above and a dithiol represented by general formula (III) above in the presence of a base.

Said dithiol is exemplified by 1,2-ethanedithiol and bis(2-mercaptoethyl) sulfide; the amount of dithiol used is normally 3 to 30 times, preferably 6 to 20 times by molar ratio, that of bis(4-halogenomethylphenyl) sulfide. Relative amounts less than 3 times are undesirable, because oligomer components tend to occur as byproducts.

Useful bases include tertiary amines, such as trimethylamine, triethylamine, tripropylamine, tributylamine and N,N-dimethylaniline; pyridines, such as pyridine and 2,6-dimethylpyridine; metal hydroxides, such as sodium hydroxide and potassium hydroxide; metal carbonates, such as sodium carbonate and potassium carbonate; and metal alcoholates, such as sodium methylate, sodium ethylate and potassium tert-butylate.

The amount of base used is normally 2 to 5 times, preferably 2 to 3 times by molar ratio, that of bis(4-halogenomethylphenyl) sulfide.

Reaction temperature is normally −10° to 150° C., preferably 0° to 100° C. Reaction temperatures exceeding 150° C. are undesirable, because increased amounts of byproducts occur, resulting in decreased percent recovery of the desired novel dithiol compound and increased coloring.

Also, in this reaction, an excess of dithiol also serves as a reaction solvent, but an organic solvent may be used in combination. Useful organic solvents include hydrocarbons, such as toluene, xylene, hexane and cyclohexane; and halogenated hydrocarbons, such as methylene chloride, chloroform, 1,2-dichloroethane, monochlorobenzene and o-dichlorobenzene.

In addition to the first embodiment described above, the novel sulfur-containing compound represented by general formula (I) above wherein R is a hydrogen atom, can be synthesized by the method schematized by the following formula (second embodiment):

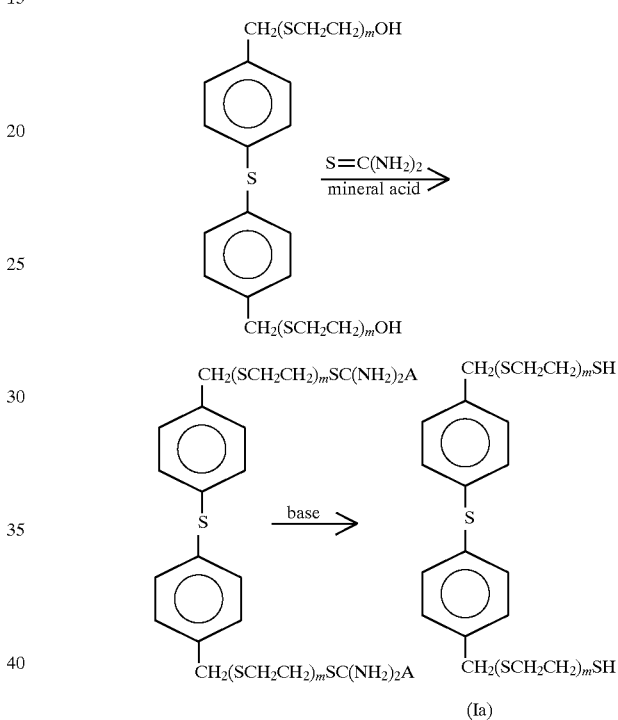

wherein m represents an integer of 1 or 2; X represents a chlorine atom, a bromine atom or an iodine atom; A represents the anion moiety of a salt formed with a mineral acid, such as hydrochloric acid, sulfuric acid, phosphoric acid or hydrogen bromide.

Specifically, the desired novel sulfur-containing compound can be obtained by reacting a bis(4-halogenomethylphenyl) sulfide represented by general formula (II) above and a mercaptoalcohol represented by general formula (IV) above in the presence of a base, then converting the reaction product into an isothiuronium salt by reaction with thiourea in the presence of a mineral acid, and subsequently hydrolyzing the salt. Here, the base may be in the form of a salt previously formed with the mercaptoalcohol represented by general formula (IV).

Said mercaptoalcohol is exemplified by 2-mercaptoethanol and 2-(2-mercaptoethylthio)ethanol; the amount of mercaptoalcohol used is normally 2 to 5 times, preferably 2 to 3 times by molar ratio, that of bis(4-halogenomethylphenyl) sulfide.

Useful bases include the above-mentioned tertiary amines, pyridines, metal hydroxides, metal carbonates and metal alcoholates. The amount of base used is normally 2 to 5 times, preferably 2 to 3 times by molar ratio, that of bis(4-halogenomethylphenyl) sulfide.

Reaction temperature with mercaptoalcohol is normally −10° to 150° C., preferably 0° to 100° C. At reaction temperatures exceeding 150° C., increased amounts of byproducts occur, resulting in decreased percent recovery of the desired novel sulfur-containing compound and increased coloring.

Useful organic solvents for this reaction include the above-mentioned hydrocarbons and halogenated hydrocarbons. Also, as phase transfer catalysts, quaternary ammonium salts, such as tetra-n-butylammonium bromide, for example, can be used.

The amount of thiourea used to form an isothiuronium salt is normally 2 to 8 times, preferably 2 to 6 times by molar ratio, that of bis(4-halogenomethylphenyl) sulfide. Useful mineral acids for this purpose include hydrochloric acid, sulfuric acid, phosphoric acid and hydrogen bromide; the amount of mineral acid used is normally 2 to 12 times, preferably 2 to 8 times by molar ratio, that of bis(4-halogenomethylphenyl) sulfide. Reaction temperature for isothiuronium salt formation is 20° to 120° C., preferably 40° to 110° C.

Also, useful solvents for this reaction include the above-mentioned hydrocarbons and halogenated hydrocarbons.

Hydrolysis is normally carried out in the presence of a base. Useful bases include the above-mentioned tertiary amines, metal hydroxides, metal carbonates and metal alcoholates ammonia, as well as primary or secondary amines, such as monomethylamine, monoethylamine, monobutylamine, dimethylamine, diethylamine and dibutylamine. The amount of base used is normally 2 to 12 times, preferably 2 to 8 times by molar ratio, that of bis(4-halogenomethylphenyl) sulfide. Reaction temperature is normally 30° to 120° C., preferably 40° to 110° C.

The novel sulfur-containing compound of the present invention, represented by general formula (I) above, wherein R is a vinyl group, a methacryloyl group, a vinylbenzyl group, a glycidyl group, an acryloyl group or an allyl group, can be synthesized by, for example, the method schematized by the following formula (third embodiment):

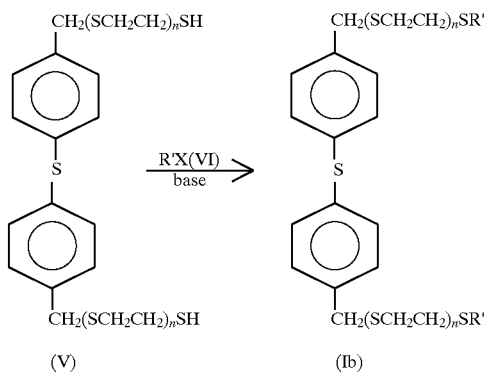

wherein n represents an integer from 0 to 2; R' represents a vinyl group, a methacryloyl group, a vinylbenzyl group, a glycidyl group, an acryloyl group or an allyl group; X represents a chlorine atom, a bromine atom or an iodine atom.

Specifically, the desired novel sulfur-containing compound can be obtained by reacting a dithiol represented by general formula (V) above, which contains an aromatic ring, and a halogen derivative represented by general formula (VI) above in the presence of a base. Here, the base may be in the form of a salt previously formed with the dithiol represented by general formula (V), which contains an aromatic ring.

The dithiol of general formula (V) above wherein n is 0 can, for example, be obtained by reacting a bis(4-halogenomethylphenyl) sulfide and thiourea, and subsequently hydrolyzing the reaction product.

Said halogen derivative is exemplified by vinyl chloride, vinyl bromide, vinyl iodide, methacrylic chloride, methacrylic bromide, chloromethylstyrene, bromomethylstyrene, iodomethylstyrene, epichlorohydrin, epibromohydrin, acrylic chloride, acrylic bromide, allyl chloride, allyl bromide and allyl iodide.

The amount of halogen derivative used is normally 2 to 8 times, preferably 2 to 6 times by molar ratio, that of the dithiol of general formula (V).

Useful bases include the above-mentioned tertiary amines, pyridines, metal hydroxides, metal carbonates and metal alcoholates; the amount of base used is normally 2 to 12 times, preferably 2 to 8 times by molar ratio, that of the dithiol of general formula (V).

Also, useful solvents include the above-mentioned hydrocarbons and halogenated hydrocarbons, as well as polar solvents, such as dimethyl sulfoxide, sulfolane, N,N-dimethylformamide, N,N-dimethylacetamide, N-methylpyrrolidone and ethylene glycol.

Reaction temperature is −10° to 200° C., preferably 0° to 150° C. Also, as phase transfer catalysts, quaternary ammonium salts, such as tetra-n-butylammonium bromide, for example, can be used. Furthermore, to prevent thiol group oxidation under alkaline conditions, a reducing agent, e.g., sodium borohydride, can also be used.

In the third embodiment, when R in general formula (I) above is a methacryloyl group, not only halogen derivatives represented by general formula (VI) but also methacrylic anhydride etc., for example, can be used to introduce R.

When R in general formula (I) above is a vinyl group, the sulfur-containing compound of the present invention can also be synthesized by the method schematized by the following formula (fourth embodiment):

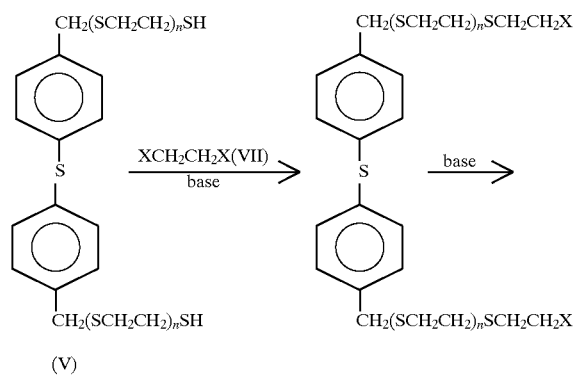

-continued

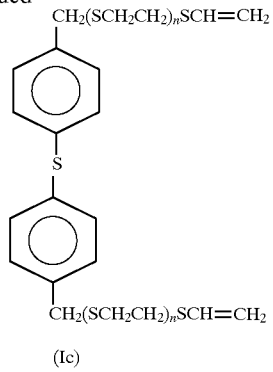

(Ic)

wherein n represents an integer from 0 to 2; the two X radicals, whether identical or not, represent a chlorine atom, a bromine atom or an iodine atom.

Specifically, the desired sulfur-containing compound can be obtained by reacting a dithiol represented by general formula (V) above, which contains an aromatic ring, and a dihalogenoethane represented by general formula (VII) in the presence of a base, and subsequently removing the halogenated hydrogen in the presence of a base. The base for the first reaction may be in the form of a salt previously formed with the dithiol represented by general formula (V), which contains an aromatic ring.

Said dihalogenoethane is exemplified by dichloroethane, chlorobromoethane, dibromoethane and diiodoethane; the amount of dihalogenoethane used is normally 2 to 30 times, preferably 6 to 20 times by molar ratio, that of dithiol. This dihalogenoethane also serves as a reaction solvent. The above-mentioned hydrocarbons and halogenated hydrocarbons can also be used as reaction solvents.

Useful bases include the above-mentioned tertiary amines, metal hydroxides, metal carbonates and metal alcoholates. The amount of base used is normally 2 to 5 times, preferably 2 to 3 times by molar ratio, that of dithiol.

Reaction temperature is −10° to 150° C., preferably 0° to 80° C. Also, as phase transfer catalysts, quaternary ammonium salts, such as tetra-n-butylammonium bromide, for example, can be used. Furthermore, a reducing agent, e.g., sodium borohydride, can also be used.

The useful base for dehydrohalogenation is exemplified by the same bases as those mentioned above; the amount of base used is normally 2 to 8 times, preferably 2 to 5 times by molar ratio, that of dithiol. In this case, good results are obtained by the use of one of the above-mentioned polar solvents, such as dimethyl sulfoxide and N,N-dimethylformamide.

Reaction temperature is −10° to 120° C., preferably 0° to 80° C.

The novel sulfur-containing compound of the present invention can be homopolymerized or copolymerized to yield polymers for optical materials, paints, adhesives, sealants, etc.

Examples of compounds copolymerizable with the novel sulfur-containing compound of the present invention, represented by general formula (I) above, include monomers and oligomers having a vinyl group, monomers and oligomers having an epoxy group, monomers having an isocyanate group, monomers having an isothiocyanate group, and monomers and oligomers having a thiol group. According to the purpose of use, not only monofunctional compounds but also multifunctional compounds can be chosen, and these compounds may be used in combination of two or more kinds.

Examples of monomers and oligomers having a vinyl group include styrene, divinylbenzene, methyl(meth) acrylate, diethylene glycol dimethacrylate, tripropylene glycol di(meth)acrylate and glycidyl (meth)acrylate. Examples of monomers and oligomers having an epoxy group include phenyl glycidyl ether, 2-ethylhexyl glycidyl ether and bisphenol A glycidyl ether. Examples of monomers having an isocyanate group include xylylene diisocyanate, dichlorodiphenyl diisocyanate, hexamethylene diisocyanate and bis(isocyanatomethyl)cyclohexane. Examples of monomers having an isothiocyanate group include xylylene diisothiocyanate, dichlorodiphenyl diisothiocyanate, hexamethylene diisothiocyanate and bis(isothiocyanatomethyl) cyclohexane. Examples of monomers and oligomers having a thiol group include 1,3-benzenedithiol, 1,4-benzenedithiol, bis(4-mercaptophenyl) sulfide, 1,2-ethanedithiol and pentaerythritol tetrakismercaptopropionate.

A composition containing one of the above-mentioned monomers and oligomers copolimerizable with the novel sulfur-containing compound of the present invention can be copolymerized by an ordinary method using heat, light, or the like.

Because the refractive index of the novel sulfur-containing compound of the present invention is not less than 1.60, the hardened product obtained by copolymerization of the above-described composition can have a refractive index as high as not less than 1.60 by choosing appropriate partner monomer etc.

The present invention is hereinafter described in more detail by means of the following examples, which are not to be construed as limitative.

EXAMPLE 1

Preparation of 4,4'-bis(4-mercapto-2-thiabutyl)phenyl sulfide (general formula (I) wherein n=1 and R=hydrogen atom) (first embodiment)

Into a 1 liter four-necked flask equipped with a mechanical stirrer, thermometer, dripping funnel and condenser, 186.1 g (0.5 mol) of bis(4-bromomethylphenyl) sulfide and 706.4 g (7.5 mol) of 1,2-ethanedithiol were sequentially placed. Next, 116.4 g (1.15 mol) of triethylamine was added drop by drop over a period of 2 hours, while the reaction temperature was kept at 0° to 10° C. After completion of the dropwise addition, the reaction mixture was further stirred at room temperature for 2 hours. After 200 g of 5% hydrochloric acid was added, organic layer was separated; the organic layer obtained was thrice washed with 200 g of water. The 1,2-ethanedithiol was distilled off from the organic layer obtained to yield 197 g of a concentrate, which was then recrystallized from 500 g of toluene/500 g of n-hexane to yield a white solid.

Structural analysis of this novel dithiol compound was conducted. The results are shown below.

Melting point 65.4° to 66.2° C.; Refractive index (70° C.) $n_D$=1.647; Measured with Abbe's refractometer (manufactured by Atago, Type 4T) at 70° C.; Elemental analysis; Theoretical value (%) C: 76.46, H:4.41, S: 19.13; Actual value (%) C: 76.44, H:4.37, S: 19.19; Infrared absorption spectrum (KBr cm$^{-1}$); 2920, 2520, 1595, 1493, 1427, 1400, 1196, 1014, 823, 688, 499; $^1$H-Nuclear magnetic resonance spectrum (CDCl$_3$, TMS reference) δ (ppm); 7.26 (S, 8H, —C$_6$H$_4$—); 3.70 (S, 4H, —SCH$_2$C$_6$H$_4$—); 2.68 (S, 4H, HSCH$_2$CH$_2$S—); 2.63 (S, 4H, HSCH$_2$CH$_2$S—); 1.77 to 1.50 (m, 2H, —SH)

These analytical results identified the white solid as 4,4'-bis(4-mercapto-2-thiabutyl)phenyl sulfide. The yield was 165 g, the percent recovery being 82% relative to the starting material bis(4-bromomethylphenyl) sulfide.

EXAMPLE 2
Preparation of 4,4'-bis(4-mercapto-2-thiabutyl)phenyl sulfide (general formula (I) wherein n=1 and R=hydrogen atom) (second embodiment)

Into a 300 ml four-necked flask equipped with a mechanical stirrer, thermometer, dripping funnel and condenser, 105.6 g (0.66 mol) of a 25% aqueous solution of sodium hydroxide was charged; 49.2 g (0.63 mol) of 2-mercaptoethanol was added drop by drop via the dripping funnel over a period of 15 minutes, while the reaction temperature was kept below 40° C. The reaction temperature was then raised to 80° C. and the reaction mixture was further stirred for 1 hour. The reaction mixture was subsequently cooled to room temperature. Next, into a 1 liter four-necked flask equipped with a mechanical stirrer, thermometer, dripping funnel and condenser, 85.0 g (0.3 mol) of bis(4-chloromethylphenyl) sulfide, 9.7 g (0.03 mol) of tetra-n-butylammonium bromide and 400 g of toluene were charged; the previously prepared aqueous solution of 2-mercaptoethanol Na salt was added drop by drop via the dripping funnel over a period of 1 hour, while the reaction temperature was kept at 10° to 20° C., followed by stirring at the same temperature for 2 hours.

While the reaction temperature was kept below 40° C., 125 g (1.2 mol) of 35% hydrochloric acid and 68.5 g (0.9 mol) of thiourea were added to this reaction mixture, followed by stirring at 92° C. for 4 hours. After the reaction mixture was cooled to room temperature, 122 g (1.22 mol) of a 40% aqueous solution of sodium hydroxide was added, while the reaction temperature was kept below 50° C., after which the reaction mixture was stirred at 92° C. for 1 hour. After the reaction mixture was cooled to room temperature and 100 g of water was added, organic layer was separated; the organic layer obtained was washed with 150 g of 35% hydrochloric acid and thrice washed with 300 g of water sequentially. The toluene was distilled off to yield 108 g of a concentrate, which was then recrystallized from 300 g of toluene/300 g of n-hexane to yield a white solid.

Structural analysis of this novel dithiol compound was conducted. The similar results to Example 1 are obtained.

The above analytical results identified the white solid as 4,4'-bis(4-mercapto-2-thiabutyl)phenyl sulfide. The yield was 90 g, which was 75% relative to the starting material bis(4-chloromethylphenyl) sulfide.

EXAMPLE 3
Preparation of 4,4'-bis(7-mercapto-2,5-dithiaheptyl)phenyl sulfide (general formula (I) wherein n=2 and R=hydrogen atom) (first embodiment)

Into a 1 liter four-necked flask equipped with a mechanical stirrer, thermometer, dripping funnel and condenser, 771.5 g (5.0 mol) of bis(2-mercaptoethyl) sulfide and 95.1 g (0.94 mol) of triethylamine were placed sequentially. Next, 148.8 g (0.4 mol) of bis(4-bromomethylphenyl) sulfide was added over a period of 2 hours, while the reaction temperature was kept at 0° to 10° C. After completion of the addition, the reaction mixture was further stirred at room temperature for 2 hours. After 200 g of 5% hydrochloric acid was added, organic layer was separated; the organic layer obtained was thrice washed with 200 g of water. The bis(2-mercaptoethyl) sulfide was distilled off from the organic layer obtained to yield 204 g of a concentrate, which was then recrystallized from 500 g of toluene/500 g of cyclohexane to yield a white solid.

Structural analysis of this novel dithiol compound was conducted. The results are shown below.

Melting point 66.8° to 67.8° C.; Refractive index (70° C.) $n_D$=1.644; Elemental analysis Theoretical value (%) C: 69.41, H:4.86, S: 25.73; Actual value (%) C: 69.38, H:4.85, S: 25.77; Infrared absorption spectrum (KBr cm$^{-1}$); 2919, 2522, 1597, 1492, 1421, 1402, 1194, 1014, 823, 678, 498; $^1$H-Nuclear magnetic resonance spectrum (CDCl$_3$, TMS reference) δ (ppm); 7.27 (S, 8H, —C$_6$H$_4$—); 3.72 (S, 4H, —SCH$_2$C$_6$H$_4$—); 2.71 (S, 4H, HSCH$_2$CH$_2$S—); 2.64 (S, 12H, HSCH$_2$CH$_2$SCH$_2$CH$_2$S—); 1.85 to 1.56 (m, 2H, —SH);

These analytical results identified the white solid as 4,4'-bis(7-mercapto-2,5-dithiaheptyl)phenyl sulfide. The yield was 176 g, which was 85% relative to the starting material bis(4-bromomethylphenyl) sulfide.

EXAMPLE 4
Preparation of 4,4'-bis(ethenylthiomethyl)phenyl sulfide (general formula (I) wherein n=0 and R=vinyl group) (fourth embodiment)

Into a 500 ml four-necked flask equipped with a mechanical stirrer, thermometer and condenser, 111.4 g (0.40 mol) of bis(4-mercaptomethylphenyl) sulfide, 271 g 0.88 mol) of a 13% aqueous solution of sodium hydroxide and 1.5 g (0.04 mol) of sodium borohydride were charged, followed by stirring at 80° to 85° C. for 4 hours. Next, into a 1 liter four-necked flask equipped with a mechanical stirrer, thermometer and condenser, 600 g (6.1 mol) of 1,2-dichloroethane and 6.5 g (0.02 mol) of tetra-n-butylammonium bromide were charged; the previously prepared aqueous solution of bis(4-mercaptomethylphenyl) sulfide Na salt was added drop by drop over a period of 2 hours, while the reaction temperature was kept at 22° to 26° C. After completion of the dropwise addition, the reaction mixture was stirred at the same temperature for 3 hours. Organic layer was then separated; the organic layer obtained was twice washed with 300 g of water, after which it was concentrated to yield 153.3 g of a white solid concentrate.

Next, into a 2 liter four-necked flask equipped with a mechanical stirrer, thermometer, dripping funnel and condenser, this concentrate and 500 g of dimethyl sulfoxide were charged; 270 g (1.4 mol) of a 28% sodium methylate-methanol solution was added drop by drop via the dripping funnel over a period of 1.5 hours, while the reaction temperature was kept at 20° to 25° C. After completion of the dropwise addition, the reaction mixture was stirred at the same temperature for 2 hours. After completion of the reaction, 600 g of cyclohexane and 450 g of water were added to the reaction mixture; organic layer was then separated; the organic layer obtained was thrice washed with 300 g of water, after which it was concentrated and purified by column chromatography to yield a colorless transparent liquid.

Structural analysis of this novel vinyl compound was conducted. The results are shown below.

Refractive index (20° C.) $n_D$=1.667; Elemental analysis Theoretical value (%) C: 65.41, H:5.49, S: 29.10; Actual value (%) C: 66.11, H:5.57, S: 28.32; Infrared absorption spectrum (NaClcm$^{-1}$); 3020, 2919, 1583, 1491, 1419, 1402, 1274, 1240, 1197, 1083, 1014, 956, 866, 831, 738, 734, 715; $^1$H-Nuclear magnetic resonance spectrum (CDCl$_3$, TMS reference) δ (ppm); 7.23 (S, 8H, —C$_6$H$_4$—); 6.31 (dd, J=10 Hz, 17 Hz, 2H, CH$_2$=CHS—); 5.16 (d, J=10 Hz, 2H, H$_{trans}$CH=CHS—); 5.12 (d, J=17 Hz, 2H, H$_{cis}$CH=CHS—); 3.84 (S, 4H, —SCH$_2$C$_6$H$_4$—)

These analytical results identified the colorless transparent liquid as 4,4'-bis(ethenylthiomethyl)phenyl sulfide. The yield was 112.4 g, which was 85% relative to the starting material bis(4-mercaptomethylphenyl) sulfide.

EXAMPLE 5
Preparation of 4,4'-bis(4-ethenylthio-2-thiabutyl)phenyl sulfide (general formula (I) wherein n=1 and R=vinyl group) (fourth embodiment)

With replacing 111.4 g (0.40 mol) of bis(4-mercaptomethylphenyl) sulfide with 159.5 g of 4,4'-bis(4-mercapto-2-thiabutyl)phenyl sulfide, the same reaction and purification as in Example 4 were carried out to yield a colorless transparent liquid.

Structural analysis of this novel vinyl compound was conducted. The results are shown below.

Refractive index (20° C.) $n_D$=1.662; Elemental analysis Theoretical value (%) C: 58.62, H:5.82, S: 35.56; Actual value (%) C: 58.92, H:5.97, S: 35.11; Infrared absorption spectrum (NaClcm$^{-1}$) 2915, 1583, 1490, 1423, 1402, 1265, 1240, 1197, 1084, 1081, 1014, 958, 867, 829; $^1$H-Nuclear magnetic resonance spectrum (CDCl$_3$, TMS reference) δ (ppm) 7.30 (S, 8H, —C$_6$H$_4$—); 6.27 (dd, J=10 Hz, 17 Hz, 2H, CH$_2$=CHS—); 5.20 (d, J=10 Hz, 2H, H$_{trans}$ CH=CHS—); 5.10 (d, J=17 Hz, 2H, H$_{cis}$CH=CHS—); 3.73 (S, 4H, —SCH$_2$C$_6$H$_4$—); 2.59 to 2.90 (m, 8H, —SCH$_2$CH$_2$S—)

These analytical results identified the colorless transparent liquid as 4,4'-bis(4-ethenylthio-2-thiabutyl)phenyl sulfide. The yield was 147.8 g, which was 82% relative to the starting material 4,4'-bis(4-mercapto-2-thiabutyl)phenyl sulfide.

EXAMPLE 6

Preparation of 4,41-bis(7-ethenylthio-2,5-dithiaheptyl) phenyl sulfide (general formula (I) wherein n=2 and R=vinyl group) (fourth embodiment)

With replacing 111.4 g (0.40 mol) of bis(4-mercaptomethylphenyl) sulfide with 207.6 g (0.40 mol) of 4,4'-bis(7-mercapto-2,5-dithiaheptyl)phenyl sulfide, the same reaction as in Example 4 and purification by recrystallization were carried out to yield a white solid.

Structural analysis of this novel vinyl compound was conducted. The results are shown below.

Melting point 62.5° to 64.4° C.; Refractive index (70° C.) $n_D$=1.635; Elemental analysis; Theoretical value (%) C: 54.69, H:6.00, S: 39.30; Actual value (%) C: 55.25, H:6.20, S: 38.55; Infrared absorption spectrum (NaClcm$^{-1}$); 2915, 1583, 1490, 1420, 1402, 1267, 1240, 1197, 1084, 1081, 1014, 957, 867, 830; $^1$H-Nuclear magnetic resonance spectrum (CDCl$_3$, TMS reference) δ (ppm) 7.30 (S, 8H, —C$_6$H$_4$—); 6.26 (dd, J=10 Hz, 17 Hz, 2H, CH$_2$=CHS—); 5.19 (d, J=10 Hz, 2H, H$_{trans}$ CH=CHS—); 5.09 (d, J=17 Hz, 2H, H$_{cis}$CH=CHS—); 3.72 (S, 4H, —SCH$_2$C$_6$H$_4$—); 2.57 to 2.91 (m, 16H, —SCH$_2$CH$_2$S—)

These analytical results identified the white solid as 4,4'-bis(7-ethenylthio-2,5-dithiaheptyl)phenyl sulfide. The yield was 178.1 g, which was 78% relative to the starting material 4, 4'-bis(7-mercapto-2,5-dithiaheptyl)phenyl sulfide.

EXAMPLE 7

Preparation of 4,4'-bis(7-ethenylthio-2,5-dithiaheptyl) phenyl sulfide (general formula (I) wherein n=2 and R=vinyl group) (third embodiment)

Into a 500 ml SUS302 autoclave equipped with a mechanical stirrer, 103.8 g (0.20 mol) of 4,4'-bis(7-mercapto-2,5-dithiaheptyl)phenyl sulfide, 64.2 g (0.60 mol) of vinyl bromide, 24.7 g (0.44 mol) of potassium hydroxide and 200 g of N,N-dimethylformamide were charged, followed by heating to 100° C. using an electric heater and subsequent stirring for 1 hour. After completion of the reaction, the reaction mixture was poured into 500 g of water and extracted with 300 g of cyclohexane; the organic layer obtained was washed with 150 g of water five times, after which it was concentrated and purified by recrystallization to yield a white solid.

Structural analysis of this novel vinyl compound was conducted. The results are the same as those obtained in Example 6.

These analytical results identified the white solid as 4,4'-bis(7-ethenylthio-2,5-dithiaheptyl)phenyl sulfide. The yield was 92.5 g, which was 81% relative to the starting material 4, 4'-bis(7-mercapto-2,5-dithiaheptyl)phenyl sulfide.

EXAMPLE 8

Preparation of 4,4'-bis(methacryloylthiomethyl)phenyl sulfide (general formula (I) wherein n=0 and R=methacryloyl group) (third embodiment)

Into a 2 liter four-necked flask equipped with a mechanical stirrer, thermometer, dripping funnel and condenser, 69.7 g (0.25 mol) of bis(4-mercaptomethylphenyl) sulfide and 67.9 g (0.65 mol) of methacrylic chloride, and 750 g of cyclohexane were placed sequentially. Next, 76 g (0.75 mol) of triethylamine was added drop by drop over a period of 20 minutes, while the reaction temperature was kept at 0° to 10° C. After completion of the dropwise addition, the reaction mixture was further stirred at the same temperature for 2 hours. After the completion of the reaction, 400 g of 5% hydrochloric acid was added and stirred for 5 minutes with keeping the temperature of the mixture below 20° C., and then organic layer was separated. The organic layer obtained was thrice washed with 300 g of water. Then, the organic layer was concentrated and purified by column chromatography to yield a colorless transparent liquid.

Structural analysis of this novel methacrylic acid derivative was conducted. The results are shown below.

Refractive index (20° C.) $n_D$=1.621; Elemental analysis; Theoretical value (%) C: 63.73, H:5.35, S: 23.20, 0:7.72; Actual value (%) C: 64.23, H:5.54, S: 22.23; Infrared absorption spectrum (NaClcm$^{-1}$); 2923, 1784, 1724, 1662, 1630, 1491, 1448, 1408, 1284, 1028, 991, 974, 894, 829; $^1$H-Nuclear magnetic resonance spectrum (CDCl$_3$, TMS reference) δ (ppm); 7.24 (S, 8H, —C$_6$H$_4$—); 6.06 (S, 2H, H$_{cis}$(to —COS—) CH=C(CH$_3$)COS—); 5.58 (S, 2H, H$_{trans}$CH=(CH$_3$)COS—); 4.71 (S, 4H, —SCH$_2$CH$_6$H$_4$—); 1.98 (S, 6H, —CH$_3$)

These analytical results identified the colorless transparent liquid as 4,4'-bis(methacryloylthiomethyl)phenyl sulfide. The yield was 99.5 g, which was 96% relative to the starting material bis(4-mercaptomethylphenyl) sulfide.

EXAMPLE 9

Preparation of 4,4'-bis(4-methacryloylthio-2-thiabutyl) phenyl sulfide (general formula (I) wherein n=1 and R=methacryloyl group) (third embodiment)

Into a 500 ml four-necked flask equipped with a mechanical stirrer, thermometer and condenser, 30 g (0.75 mol) of sodium hydroxide, 0.47 g (0.0125 mol) of sodium borohydride, 99.7 g (0.25 mol) of 4,4'-bis(4-mercapto-2-thiabutyl)phenyl sulfide and 270 g of water were charged, followed by stirring at 80° to 85° C. for 4 hours. Next, into a 2 liter four-necked flask equipped with a mechanical stirrer, thermometer, dripping funnel and condenser, 67.9 g (0.65 mol) of methacrylic chloride, 750 g of cyclohexane and 4.0 g (0.0125 mol) of tetra-n-butylammonium bromide were charged; the previously prepared aqueous solution of 4,4'-bis(4-mercapto-2-thiabutyl)phenyl sulfide Na salt was added drop by drop over a period of 20 minutes, while the reaction temperature was kept at 0° to 20° C. After completion of the dropwise addition, the reaction mixture was stirred at room temperature for 2 hours. Organic layer was then separated; the organic layer obtained was thrice washed with 300 g of water, after which it was concentrated and purified by column chromatography to yield a colorless transparent liquid.

Structural analysis of this novel methacrylic acid derivative was conducted. The results are shown below.

Refractive index (20° C.) $n_D$=1.614; Elemental analysis; Theoretical value (%) C: 58.39, H:5.65, S: 29.97, 0:5.99; Actual value (%) C: 58.80, H:5.74, S: 29.46; Infrared absorption spectrum (NaClcm$^{-1}$); 2921, 1784, 1662, 1630, 1491, 1448, 1403, 1284, 1028, 991, 973, 935, 893, 829; $^1$H-Nuclear magnetic resonance spectrum (CDCl$_3$, TMS reference) δ (ppm); 7.27 (S, 8H, —C$_6$H$_4$—); 6.06 (S, 2H, H$_{cis}$(to —COS—) CH═C(CH$_3$)COS—); 5.59 (S, 2H, H$_{trans}$CH═C(CH$_3$)COS—); 3.76 (S, 4H, —SCH$_2$C$_6$H$_4$—); 3.10 (dd, J=6 Hz, 9 Hz, 4H, COSCH$_2$—); 2.62 (dd, J=6 Hz, 9 Hz, 4H, —CH$_2$SCH$_2$C$_6$H$_4$); 1.96 (S, 6H, —CH$_3$)

These analytical results identified the colorless transparent liquid as 4,4'-bis(4-methacryloylthio-2-thiabutyl)phenyl sulfide. The yield was 117.7 g, which was 88% relative to the starting material 4,4'-bis(4-mercapto-2-thiabutyl)phenyl sulfide.

EXAMPLE 10

Preparation of 4,4'-bis[4-(4-vinylbenzylthio)- 2-thiabutyl)phenyl sulfide (general formula (I) wherein n=1 and R=vinyl benzyl group) (third embodiment)

Into a 2 liter four-necked flask equipped with a mechanical stirrer, thermometer, dripping funnel and condenser, 79.7 g (0.20 mol) of 4,4'-bis(4-mercapto-2-thiabutyl)phenyl sulfide, 67.2 g (0.44 mol) of p-chloromethylstyrene and 400 g of toluene were sequentially placed. Next, 176 g (0.44 mol) of 10% sodium hydroxide aqueous solution was added drop by drop via the dripping funnel over a period of 1 hour, while the reaction temperature was kept at 35° to 40° C. After completion of the dropwise addition, the reaction mixture was further stirred at the same temperature for 1.5 hours. After 400 g of toluene was added, organic layer was separated at 40° C.; the organic layer obtained was twice washed with 400 g of water at 40° C. The organic layer was cooled to 0° C. and the white solid precipitated was filtered off, dried and recrystallized from 600 g of toluene/250 g of ethanol to yield a white solid.

Structural analysis of this novel vinylbenzyl compound was conducted. The results are shown below.

Melting point 121.9° to 122.8° C.; Elemental analysis; Theoretical value (%) C: 68.53, H:6.07, S: 25.40; Actual value (%) C: 68.60, H:6.12, S: 25.28; Infrared absorption spectrum (KBr cm$^{-1}$); 2919, 1627, 1594, 1510, 1492, 1402, 1193, 1014, 991, 904, 847, 825, 687, 521, 498; $^1$H-Nuclear magnetic resonance spectrum (CDCl$_3$, TMS reference) δ (ppm); 7.11 to 7.39 (m, 16H, —C$_6$H$_4$—); 6.68 (dd, J=11 Hz, 17 Hz, 2H, CH$_2$═CHS—); 5.72 (d, J=17 Hz, 2 Hz, H$_{cis}$CH═CHC$_6$H$_4$—); 5.23 (d, J=10 Hz, 2H, H$_{trans}$CH═CHC$_6$H$_4$ —); 3.67 (S, 4H, —CH$_2$C$_6$H$_4$S—); 3.64 (S, 4H, —CH$_2$C$_6$H$_4$CH═CH$_2$); 2.56 (S, 8H, —SCH$_2$CH$_2$S—)

These analytical results identified the white solid as 4,4'-bis[4-(4-vinylbenzylthio)-2-thiabutyl)phenyl sulfide. The yield was 101.0 g, which was 80% relative to the starting material 4,4'-bis(4-mercapto-2-thiabutyl)phenyl sulfide.

EXAMPLE 11

Preparation of 4,4'-bis(2,3-epoxypropylthiomethyl)phenyl sulfide (general formula (I) wherein n=0 and R=glycidyl group) (third embodiment)

In a 2 liter four-necked flask equipped with a mechanical stirrer, thermometer, dripping funnel and condenser, 278 g (1.0 mol) of bis(4-mercaptomethylphenyl) sulfide, 222 g (2.4 mol) of epichlorohydrine and 500 g of dioxane were placed. Next, 44 g (0.11 mol) of 10% sodium hydroxide aqueous solution was added drop by drop over a period of 1.5 hours, while the reaction temperature was kept at 10° to 30° C. The reaction mixture was further stirred with keeping the reaction temperature in the range from 20° to 30° C. for 2 hours. Then, the reaction mixture was heated up to 60° C., to which 213.5 g (2.4 mol) of 45% sodium hydroxide aqueous solution was added drop by drop over 2 hours with keeping the reaction temperature of 60° to 65° C. The stirring was continued at the same temperature for 10 hours. After the completion of the reaction, 255 g of water and 500 g of toluene was added to the reaction mixture to separate organic layer with keeping the temperature of from 60° to 55° C. The organic layer obtained was twice washed with 255 g of water. The organic layer was concentrated and purified by column chromatography to yield a colorless transparent liquid.

Structural analysis of this novel glycidyl compound was conducted. The results are shown below.

Refractive index (20° C.) $n_D$=1.645; Elemental analysis; Theoretical value (%) C: 61.50, H:5.68, S: 24.63, 0:8.19; Actual value (%) C: 61.70, H:5.60, S: 24.40; Infrared absorption spectrum (NaClcm$^{-1}$); 3049, 2989; 2916, 1595, 1562, 1491, 1402, 1263, 1236, 1200, 1130, 1084, 1014, 951, 924, 825, 758, 696; $^1$H-Nuclear magnetic resonance spectrum (CDC$_{13}$, TMS reference) δ (ppm); 7.26 (S, 8H, —C$_6$H$_4$—); 3.77 (S, 4H, —SCH$_2$C$_6$H$_4$—);

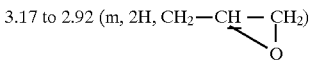

3.17 to 2.92 (m, 2H, CH$_2$—CH — CH$_2$)

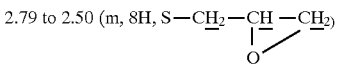

2.79 to 2.50 (m, 8H, S—CH$_2$—CH —CH$_2$)

These analytical results identified the colorless transparent liquid as 4,4'-bis(2,3-epoxypropylthiomethyl)phenyl sulfide. The yield was 351.5 g, which was 90% relative to the starting material bis(4-mercaptomethylphenyl) sulfide.

EXAMPLE 12

Preparation of 4,4'-bis(7-methacryloylthio-2,5-dithiaheptyl) phenyl sulfide (general formula (I) wherein n=2 and R=methacryloyl group) (third embodiment)

In a 2 liter four-necked flask equipped with a mechanical stirrer, thermometer, dripping funnel and condenser, 129.7 g (0.25 mol) of 4,4'-bis(7-mercapto-2,5-dithiaheptyl)phenyl sulfide, 67.9 g (0.65 mol) of methacrylic chloride and 750 g of cyclohexane were placed, to which 76 g (0.75 mol) of triethylamine was added drop by drop over a period of 20 minutes, while the reaction temperature was kept at 0° to 10° C. After completion of the dropwise addition, the reaction mixture was further stirred at the same temperature for 2 hours. After the completion of the reaction, 400 g of 5% hydrochloric acid was added to the reaction mixture with keeping the temperature of the mixture below 20° C. After the reaction mixture was stirred for 5 minutes, organic layer was separated. The organic layer was washed thrice with 300 g of water. Subsequently the organic layer was concentrated and purified by column chromatography to yield a colorless transparent liquid.

Structural analysis of this novel methacrylic acid derivative was conducted. The results are shown below.

Refractive index (20° C.) $n_D$=1.605; Elemental analysis; Theoretical value (%) C: 55.00, H:5.85, S: 34.26, 0:4.88; Actual value (%) C: 55.20, H:5.95, S: 34.01; Infrared absorption spectrum (NaClcm$^{-1}$); 2956, 2925, 1784, 1722, 1660, 1630, 1595, 1491, 1450, 1433, 1377, 1284, 1282, 1195, 1124, 1051, 1002, 976, 947, 891; $^1$H-Nuclear magnetic resonance spectrum (CDCl$_3$, TMS reference) δ (ppm); 7.27(S, 8H, —C$_6$H$_4$—); 6.07 (S, 2H, H$_{cis}$(to —COS—) CH=C(CH$_3$)COS—); 5.61 (S, 2H, H$_{trans}$CH=C(CH$_3$) COS—); 3.74 (S, 4H, —SCH$_2$CH$_6$H$_4$—); 2.58 to 3.17 (m, 16H, —SCH$_2$CH$_2$SCH$_2$CH$_2$S—); 1.99 (S, 6H, —CH$_3$)

These analytical results identified the colorless transparent liquid as 4,4'-bis(7-methacryloylthio-2,5-dithiaheptyl) phenyl sulfide. The yield was 139.27 g, which was 85% relative to the starting material 4,4$^1$-bis(7-mercapto-2,5-dithiaheptyl)phenyl sulfide.

INDUSTRIAL APPLICABILITY

The novel sulfur-containing compound of the present invention can be copolymerized with various copolymerizable compounds to yield excellent hardened products of high refractive index. The novel sulfur-containing compound of the present invention can therefore be used as a very useful monomer for the production of optical materials, paints, adhesives, sealants, etc. having excellent properties.

We claim:

1. A sulfur-containing compound represented by the following general formula (I):

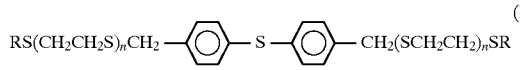

wherein n is an integer from 0 to 2; R represents a hydrogen atom, a vinyl group, a methacryloyl group, a vinylbenzyl group, a glycidyl group, an acryloyl group or an allyl group; and the case where n is 0 and R is a hydrogen atom is excluded.

2. The sulfur-containing compound according to claim 1, wherein R in the general formula (I) is a hydrogen atom, a vinyl group, a methacryloyl group, a vinylbenzyl group, or a glycidyl group.

3. A method for preparing a sulfur-containing compound represented by the following general formula (Ia):

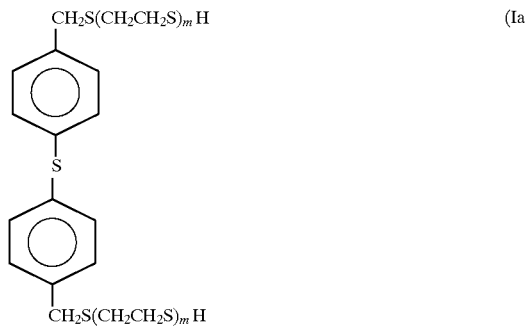

wherein m is an integer of 1 or 2, characterized by reacting, in the presence of a base, a bis(4-halogenomethylphenyl) sulfide represented by the following general formula (II):

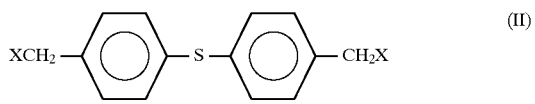

wherein X is a chlorine atom, a bromine atom or an iodine atom with a dithiol represented by the following general formula (III):

wherein m is an integer of 1 or 2.

4. A method for preparing a sulfur-containing compound represented by the following general formula (Ia):

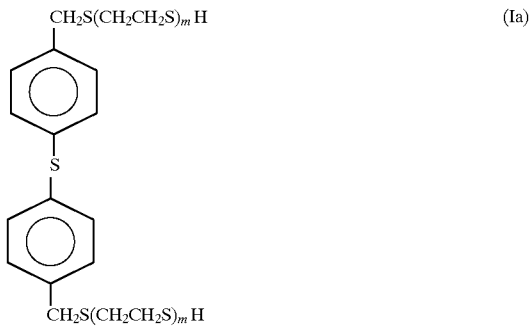

wherein m is an integer of 1 or 2, characterized by reacting, in the presence of a base, a bis(4-halogenomethylphenyl) sulfide represented by the following general formula (II):

wherein X is a chlorine atom, a bromine atom or an iodine atom with a mercaptoalcohol represented by the following general formula (IV):

wherein m is an integer of 1 or 2; treating the reaction product with thiourea in the presence of a mineral acid to form an isothiuronium salt; and hydrolyzing the salt.

5. A method for preparing a sulfur-containing compound represented by the following general formula (Ib):

wherein n is an integer from 0 to 2; R' is a vinyl group, a methacryloyl group, a vinylbenzyl group, a glycidyl group, an acryloyl group or an allyl group, characterized by reacting, in the presence of a base, an aromatic ring-containing dithiol represented by the following general formula (V):

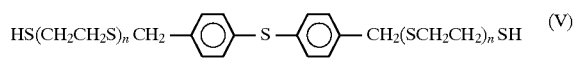

wherein n is an integer from 0 to 2 with a halogen derivative represented by the following general formula (VI):

wherein R' is a vinyl group, a methacryloyl group, a vinylbenzyl group, a glycidyl group, an acryloyl group or an allyl group; and X is an chlorine atom, a bromine atom or an iodine atom.

6. A method for preparing a sulfur-containing compound represented by the following general formula (Ic):

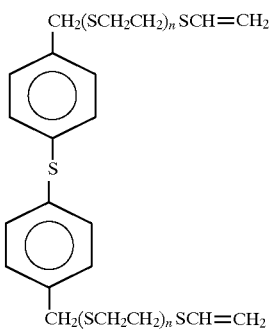

$$CH_2(SCH_2CH_2)_n SCH=CH_2 \quad (Ic)$$

$$CH_2(SCH_2CH_2)_n SCH=CH_2$$

wherein n is an integer from 0 to 2 characterized by reacting, in the presence of a base, an aromatic ring-containing dithiol represented by the following general formula (V):

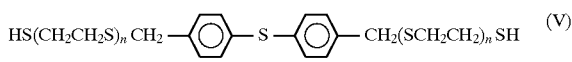

$$HS(CH_2CH_2S)_n CH_2 \text{—} \bigcirc \text{—} S \text{—} \bigcirc \text{—} CH_2(SCH_2CH_2)_n SH \quad (V)$$

wherein n is an integer from 0 to 2 with a dihalogenoethane represented by the following general formula (VII):

$$XCH_2CH_2X \quad (VII)$$

wherein each of the two X radicals, which may be identical or different, is a chlorine atom, a bromine atom or an iodine atom; and dehydrohalogenating the reaction product in the presence of a base to introduce a vinyl group at the terminal.

7. The method according to claim 3, wherein the amount of dithiol used is 3 to 30 times, by molar ratio, that of bis(4-halogenomethylphenyl)sulfide.

8. The method according to claim 3, wherein said base is selected from the group consisting of tertiary amines, pyridines, metal hydroxides, metal carbonates and metal alcoholates.

9. The method according to claim 3, wherein the amount of base used is 2 to 5 times, by molar ratio, that of bis(4-halogenomethylphenyl)sulfide.

10. The method according to claim 4, wherein the amount of mercaptoalcohol used in 2 to 5 times, by molar ratio, that of bis(4-halogenomethylphenyl)sulfide.

11. The method according to claim 4, wherein said base is selected from the group consisting of tertiary amines, pyridines, metal hydroxides, metal carbonates and metal alcoholates.

12. The method according to claim 4, wherein the amount of base used is 2 to 5 times, by molar ratio, that of bis(4-halogenomethylphenyl)sulfide.

13. The method according to claim 4, wherein said mineral acid is selected from the group consisting of hydrochloric acid, sulfuric acid, phosphoric acid and hydrogen bromide, wherein the amount of said mineral acid used is 2 to 12 times by molar ratio, that of bis(4-halogenomethylphenyl) sulfide.

14. The method according to claim 5, wherein said halogen derivative is selected from the group consisting of vinyl chloride, vinyl bromide, vinyl iodide, methacrylic chloride, methacrylic bromide, chloromethylstyrene, bromomethylstyrene, iodomethylstyrene, epichlorohydrin, epibromohydrin, acrylic chloride, acrylic bromide, allyl chloride, allyl bromide and allyl iodide.

15. The method according to claim 5, wherein the amount of halogen derivative is 2 to 8 times, by molar ratio, that of the aromatic ring-containing dithiol.

16. The method according to claim 5, wherein said base is selected from the group consisting of tertiary amines, pyridines, metal hydroxides, metal carbonates and metal alcoholates.

17. The method according to claim 5, wherein the amount of base used is 2 to 12 times, by molar ratio, that of the aromatic ring-containing dithiol.

18. The method according to claim 6, wherein said dihalogenoethane is selected from the group consisting of dichloroethane, dibromoethane and diiodoethane.

19. The method according to claim 6, wherein the amount of dihalogenoethane used is 2 to 30 times, by molar ratio, that of the aromatic ring-containing dithiol.

* * * * *